United States Patent [19]

Greaney et al.

[11] Patent Number: 5,126,465
[45] Date of Patent: Jun. 30, 1992

[54] METHOD FOR MAKING $Mo_4S_4L_6$

[75] Inventors: Mark A. Greaney, Upper Black Eddy, Pa.; Catherine L. Coyle, Mendham; Edward I. Stiefel, Bridgewater, both of N.J.

[73] Assignee: Exxon Research and Engineering Company, Florham Park, N.J.

[21] Appl. No.: 688,212

[22] Filed: Apr. 22, 1991

[51] Int. Cl.$^5$ ............................................. C07F 11/00
[52] U.S. Cl. ........................................... 556/61; 556/63
[58] Field of Search .................................... 556/61, 63

[56] References Cited

U.S. PATENT DOCUMENTS 3,668,227  6/1972  Mattucci et al. ............... 556/61 X
3,991,090  11/1976 Hagstrom et al. .............. 556/61 X
4,098,705  7/1978  Sakurai et al. ................. 556/61 X
4,259,254  3/1981  Bridger ............................ 556/61
4,266,945  5/1981  Karn ................................ 556/31 X Primary Examiner—Arthur C. Prescott
Attorney, Agent, or Firm—Joseph J. Dvorak

[57] ABSTRACT

There is provided an improved method for preparing compounds of the formula $Mo_4S_4L_6$ comprising:

heating a solution of a compound having the formula $MoL_4$, wherein L is a 1,1-dithioacid ligand, at a temperature and for a time sufficient to form the $Mo_4S_4L_6$ compound. Preferably, the $MoL_4$ compound is dissolved in an organic solvent and the solution is heated at temperatures above 25° C., up to the boiling point of the solvent and, more preferably, at temperatures in the range of from about 50° C. to about 250° C.

8 Claims, No Drawings

METHOD FOR MAKING Mo$_4$S$_4$L$_6$

FIELD OF THE INVENTION

This invention relates to improvements in the synthesis of Mo$_4$S$_4$L$_6$ compounds.

BACKGROUND OF THE INVENTION

Molybdenum compounds having a thiocubane structure are produced by a variety of methods. For example, T. Shibahara et al, *J. Am. Chem. Soc.*, Vol. 106, pp. 789-791 (1984) discusses a method for making the [Mo$_4$S$_4$(edta)$_2$]3- ion containing species by reacting a water soluble Mo(V) dimer in HCl. P. Kathirgamanathan et al, *J. Chem. Soc., Chem. Commun.* pp. 953-954 (1985), describes electrochemically reducing a Na$_2$[Mo(V)$_2$S$_2$O$_2$(cysteine)$_2$]3H$_2$O in HCl to form (Me$_4$N)$_5$-[Mo$_3$S$_4$(NCS)$_9$]and the tetramer (Me$_4$N)$_7$-[Mo$_4$S$_4$(NCS)$_{12}$]. P. Kathirgamanathan et al, *J. Chem. Soc., Chem. Commun.*, pp. 1437-1439 (1985), describes preparing mixtures of (Me$_4$N)$_5$[Mo$_3$X$_4$(NCS)$_9$]and (Me$_4$N)$_7$[Mo$_4$X$_4$(NCS)$_{12}$]compounds, where X is sulfur or oxygen. More recently, in U.S. Pat. No. 4,990,271 there is described a method for making thiocubane Mo compounds having the formula Mo$_4$S$_4$(ROCS$_2$)$_2$ by reacting molybdenum hexacarbonyl, Mo(CO)$_6$, with a xanthogen disulfide.

Notwithstanding the plethora of methods for preparing molybdenum containing thiocubane type compounds, there remains a need for a preparative method that is more simple and less expensive.

It is, therefore, an object of the present invention to provide an improved method for forming thiocubane Mo compounds of the general formula Mo$_4$S$_4$L$_6$, where L is a dithioacid ligand.

SUMMARY OF THE INVENTION

Accordingly, there is provided an improved method for preparing compounds of the formula Mo$_4$S$_4$L$_6$ comprising:

heating a solution of a compound having the formula MoL$_4$, wherein L is a 1,1-dithioacid ligand, at a temperature and for a time sufficient to form the Mo$_4$S$_4$L$_6$ compound. Preferably, the MoL$_4$ compound is dissolved in an organic solvent and the solution is heated at temperatures above 25° C., up to the boiling point of the solvent and, more preferably, at temperatures in the range of from about 50° C. to about 250° C.

DETAILED DESCRIPTION

In the method of the present invention, a compound having the formula MoL$_4$, wherein L is a 1,1-dithioacid ligand, is added to a sufficient amount of an organic solvent to form a solution.

In general, any dithioacid ligand may be used. Thus, L may be a dithiocarbamate, xanthate, dithiophosphate, dithiophosphinate, thioxanthate or other similar dithioacids and mixtures thereof. Preferably, the ligands, L, will have organo groups having from about 1 to 30 carbon atoms. For example, when L is a dithiocarbamate, (S$_2$CNR$_2$—), or a xanthate, (S$_2$COR—), the organo group R preferably will have from 1 to 30 carbon atoms.

The MoL$_4$ compound can be prepared by generally known techniques such as that described in *J. Inorg. Nucl. Chem. Lett.*, Vol. 39, p. 289 (1971) or by reacting an alkali metal salt of the dithioacid with MoCl$_4$ in a manner similar to that disclosed in *J. C. S. Dalton*, p. 1614 (1972).

Any organic solvent capable of dissolving the MoL$_4$ compound may be used in the method of this invention. In general, hydrocarbons, alcohols, ethers, chlorinated hydrocarbons and nitriles are useful. Especially useful are organic solvents that have boiling points above about 50° and in the range, for example, of from about 50° C. to about 250° C. Indeed, aromatic hydrocarbons, such as toluene, xylene and the like, are most preferred organic solvents for use in this invention.

After forming the solution of the MoL$_4$ compound, the solution is heated at a temperature and for a time sufficient to form the Mo$_4$S$_4$L$_6$ compound. In general, the solution will be heated at a temperature above room temperature up to the boiling point of the solvent. Typically, the solution will be heated at temperatures in the range of from about 50° C. to about 250° C. The time of heating will depend upon a number of factors, such as the solvent and the ligand, L, chosen and the temperature employed. In general, however, the solution will be heated for times ranging between about 1 hour to 5 days or more.

The Mo$_4$S$_4$L$_6$ product can be isolated readily from the heated solution by any number of well known techniques. In some instances, the product will precipitate from solution and, hence, can be separated and recovered by filtration. In other instances, the solvent can be removed, for example, in vacuo, and the crude product will remain. The crude product can, of course, be purified by recrystallization, column chromatography or the like.

The following examples will serve to illustrate specific procedures used in accordance with the claimed invention.

EXAMPLE 1

Preparation of Mo$_4$S$_4$(Diethyldithiocarbamate)$_6$ from Mo(Diethyldithiocarbamate)$_4$ A quantity of Mo (diethyldithiocarbamate)$_4$ (250 mg, 0.36 m mol) was added to 25 ml of degassed toluene and heated to 125° C. for 5 days. The black solid isolated by filtration is Mo$_4$S$_4$(diethyldithiocarbamate)$_6$, as confirmed by cyclic voltametry and UV-VIS spectroscopy. Yield = 75 mg, 60% based on Mo.

EXAMPLE 2

Preparation of Mo$_4$S$_4$(Octylxanthate)$_6$ from Mo(Octylxanthate)$_4$

A quantity of Mo(octylxanthate)$_4$ (200 mg, 0.2 m mol) was added to 15 ml of degassed toluene and heated to 110° C. for 4 hours. The solvent was removed under reduced pressure and the residue was extracted with 10 ml CH$_2$Cl$_2$. The product, Mo$_4$S$_4$(octylxanthate)6, was purified by column chromatography with silica as the support and 7:1 hexane/methylene chloride as the eluent. Yield = 100 mg, 37% based on Mo.

What is claimed is:

1. A method for preparing a compound having the formula Mo$_4$S$_4$L$_6$, wherein L is a dithioacid or mixtures thereof, comprising:

heating a solution of a compound having the formula MoL$_4$, wherein L is a ligand selected from dithioacid and mixtures thereof, the heating being at a temperature and for a time sufficient to form the $Mo_4S_4L_6$ compound.

2. The method of claim 1 wherein the dithioacid is selected from organo substituted dithiocarbamates, dithiophosphinates, xanthates, thioxanthates, dithiophosphates and mixtures thereof.

3. The method of claim 2 wherein the organo substituent has from about 1 to about 30 carbon atoms.

4. The method of claim 2 wherein the $MoL_4$ is dissolved in an organic solvent to form a solution.

5. The method of claim 4 wherein the solution is heated at temperatures above 25° C. up to the boiling point of the solvent.

6. The method of claim 5 wherein the solution is heated at temperatures in the rang of about 50° C. to about 250° C.

7. The method of claim 5 wherein the solvent is toluene and the solution is heated at the refluxing temperature of toluene.

8. The method of claim 6 wherein the solution is heated for about 1 hour to about 5 days.

* * * * *